United States Patent [19]
Costa et al.

[11] Patent Number: 5,488,049
[45] Date of Patent: Jan. 30, 1996

[54] METHOD OF TREATING LEARNING AND MEMORY DISORDERS USING BENZOTHIADIAZIDE DERIVATIVES AS NOOTROPIC AGENTS

[75] Inventors: Erminio Costa, Chevy Chase, Md.; Alessandro Guidotti, Washington, D.C.; Mario Baraldi, Modena, Italy; Mariella Bertolino, Washington, D.C.; Maria DiBella, Milan, Italy; Stefano Vicini, Washington, D.C.

[73] Assignee: FIDIA - Georgetown Institute for the Neuro-Sciences, Washington, D.C.

[21] Appl. No.: 164,943

[22] Filed: Dec. 10, 1993

[51] Int. Cl.$^6$ .................................................. A61K 31/505
[52] U.S. Cl. ............................................................ 514/223.2
[58] Field of Search .......................... 514/223.2; 544/12, 544/13

[56] References Cited

U.S. PATENT DOCUMENTS

| | | | |
|---|---|---|---|
| 3,111,517 | 11/1963 | McClamore et al. | 544/13 |
| 3,163,645 | 12/1964 | Stvens et al. | 544/12 |
| 3,264,292 | 8/1966 | Close | 544/13 |
| 3,275,625 | 9/1966 | Muller et al. | 544/12 |

OTHER PUBLICATIONS

Patneau, D. et al., Jour. of Neuroscience, Aug. 1993, 13(8): pp. 3496–3509.

Kerwin, R, Ph.D., EAAs and Psychosis, Excitatory Amino Acids and Psychosis, pp. 279–283. (1992).

Moerschbaecher, J. M., Ph.D., EAAs, Learning and Memory, The Role of Excitatory Amino Acids in Learning and Memory, pp. 211–214. (1992).

Ozawa, S., M.D., et al., Two Types of Responses to KA and AMPA, pp. 117–123 (1992).

M. J. Pontecorvo et al, Pharmacology Biochemistry & Behavior, vol. 22, pp. 745–752, 1985.

L. H. Werner et al, Dihydrobenzothiadiazine 1,1–Dioxides, pp. 1161–1166, 1960.

J. G. Topliss et al, Antihypertensive Agents, vol. 6, pp. 122–127, 1963.

B. Sommer et al, Science, pp. 1581–1585, 1990.

I. Ito et al, Journal of Physiology, 424, pp. 533–543, 1990.

G. J. Kant et al, Pharmacology Biochemistry & Behavior, vol. 39, pp. 479–485, 1991.

J. T. Wroblewski et al, Annu. Rev. Pharmacol. Toxicol., 1989, vol. 29, pp. 441–474.

*Primary Examiner*—Glennon H. Hollrah
*Assistant Examiner*—Mary C. Cebulak
*Attorney, Agent, or Firm*—Birch, Stewart, Kolasch & Birch

[57] ABSTRACT

The present invention is directed to the use of benzothiadiazide derivatives as nootropic agents to treat memory and learning disorders.

13 Claims, 7 Drawing Sheets

ORAL

METHOD OF TREATING LEARNING AND MEMORY DISORDERS USING BENZOTHIADIAZIDE DERIVATIVES AS NOOTROPIC AGENTS

BACKGROUND OF THE INVENTION

1. Field of the Invention

The present invention relates to the use of benzothiadiazide derivatives as nootropic agents (from the Greek "noo" to know) to treat: memory and learning disorders.

2. Description of Related Art

Heretofore, benzothiadiazide derivatives are known to exhibit diuretic and antihypertensive action.

The amino acid L-glutamate is the principal excitatory neurotransmitter in the mammalian CNS. This neurotransmitter exerts its effects by activating ionotropic and metabotropic receptors located on the dendrites and soma of neurons and glial cells.

The ionotropic glutamate receptors can be classified into three types according to their structure, conductance characteristics and selectivity for three synthetic agonists: NMDA (N-methyl-D-aspartic acid), AMPA (α-amino 2-3, dihydro-5-methyl-3-oxo-4-isoxazole propionic acid), and kainate (2-carboxy-4-(1-methylhexyl)-3-pyrrolidine acetiacid). A number of compounds that bind to these three types of ionotropic glutamate receptors have been demonstrated to facilitate or inhibit memory and learning processes in animals and humans. For example, ketamine, phencyclidine, and even more potently, dizocilpine (hereinafter "MK-801"), which are allosteric NMDA receptor antagonists, produce profound alterations in learning, disrupt memory consolidation and retrieval in animals and man, thereby eliciting a psychotic syndrome resembling schizophrenia in humans (1, 2, 3). On the other hand, aniracetam and related pyrrolidinone derivatives, by acting preferentially as positive allosteric modulators of AMPA receptor function (4,5), increase the strength of synaptic responses elicited by electrical stimulation of excitatory affferents to CA1 hippocampal pyramidal neurons attenuating AMPA receptor spontaneous desensitization (6) and enhancing learning and memory (nootropic action) in animals (7,8,9).

Based on these observations and on the clinical evidence that several neurological diseases characterized by severe learning and memory loss (i.e., brain trauma, stroke, Alzheimer's disease and senile dementia) due to an impairment of glutamatergic transmission, the present inventors studied in detail the relationship existing between nootropic drug action and increase in excitatory amino acid synaptic strength using electrophysiological, behavioral, molecular biological and immunohistochemical techniques. A goal of the present study has been to search for nootropic drugs that increase synaptic strength of excitatory synapses by potently and selectively attenuating AMPA receptor desensitization. Aniracetam is a drug that decreases AMPA receptor desensitization, but due to its low potency and short lasting action, cannot be used efficaciously in therapy. Therefore, interest has focused on the development of potent derivatives of benzothiadiazide which, by allosterically reducing spontaneous AMPA receptor desensitization, increase excitatory synaptic strength in CA1 hippocampal neurones, with a potency and duration of action that allows their use in therapy as nootropic drugs. It is also important that any such developed derivatives are able to cross the blood brain barrier in order to exert their therapeutic effect in the brain.

SUMMARY OF THE INVENTION

Further scope of the applicability of the present invention will become apparent from the detailed description and drawings provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention is directed to a method of treating memory disorders and learning disorders which comprises administering to a mammal in need of such treatment an amount effective to treat memory disorders or learning disorders of a compound having the formula:

$R^1$ is H or halogen, or $SO_2NH_2$;

$R^2$ is H or halogen;

$R^3$ is $C_1$–$C_8$ straight or branched alkyl,
  $C_2$–$C_8$ straight or branched alkenyl,
  $C_2$–$C_8$ straight or branched alkynyl,
  $C_1$–$C_8$ straight or branched alkyl, substituted with a halogen, $NH_2$, N-$C_1$–$C_4$-alkyl substituted amine, N,N'-$C_1$–$C_4$-alkyl disubstituted amine, $C_1$–$C_4$-alkoxy group, $C_1$–$C_4$-thioalkyl group, a $C_3$–$C_6$ cycloalkyl group, $C_3$–$C_6$ cycloalkenyl group, a $C_6$–$C_8$-bicycloalkyl or a $C_6$–$C_8$ bicycloalkenyl group,
  $C_2$–$C_8$ straight or branched alkenyl group substituted with a halogen, $NH_2$, N-$C_1$–$C_4$-alkyl substituted amine, N,N'-$C_1$–$C_4$-alkyl disubstituted amine, $C_1$–$C_4$-alkoxy group, $C_1$–$C_4$-thioalkyl group, a $C_3$–$C_6$ cycloalkyl group, $C_3$–$C_6$ cycloalkenyl group, a $C_6$–$C_8$-bicycloalkyl or a $C_6$–$C_8$ bicycloalkenyl group,
  $C_2$–$C_8$ straight or branched alkynyl group substituted with a halogen, $NH_2$, N-$C_1$–$C_4$-alkyl substituted amine, N,N'-$C_1$–$C_4$-alkyl disubstituted amine, $C_1$–$C_4$-alkoxy group, $C_1$–$C_4$-thioalkyl group, a $C_3$–$C_6$ cycloalkyl group, a $C_3$–$C_6$ cycloalkenyl group, a $C_6$–$C_8$-bicycloalkyl, or a $C_6$–$C_8$ bicycloalkenyl group,
  $C_3$–$C_6$ cycloalkyl,
  $C_3$–$C_6$ cycloalkenyl,
  $C_6$–$C_8$ bicycloalkyl, or
  $C_6$–$C_8$ bicycloalkenyl;

with the proviso that when $R^1$ is $SO_2NH_2$ and $R_2$ is halogen, $R_3$ is not $C_6$–$C_8$ bicycloalkenyl; or a pharmaceutically acceptable salt thereof.

The present invention is also directed to positive (+) enantiomers of the above compounds and compositions containing the same and methods of separation of the (+) enantiomer.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention, in which.

Each value is the mean ±SE of at least 15 rats. *P<0.05 when the Alprazolam treated group was compared to the other groups. Linear regression analysis of the different groups reveals that the slope is significantly different than zero (P<0.02) in all groups except in the VEH+ALP treated group, where the slope was not statistically different from zero (P<0.06).

Figure 8B:
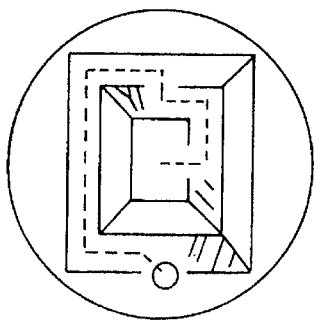
Figure 8C:
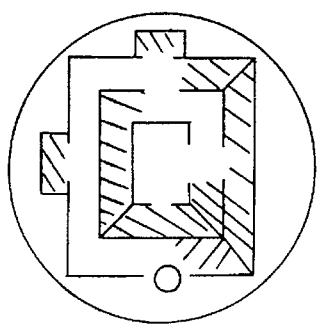
Figure 8A:
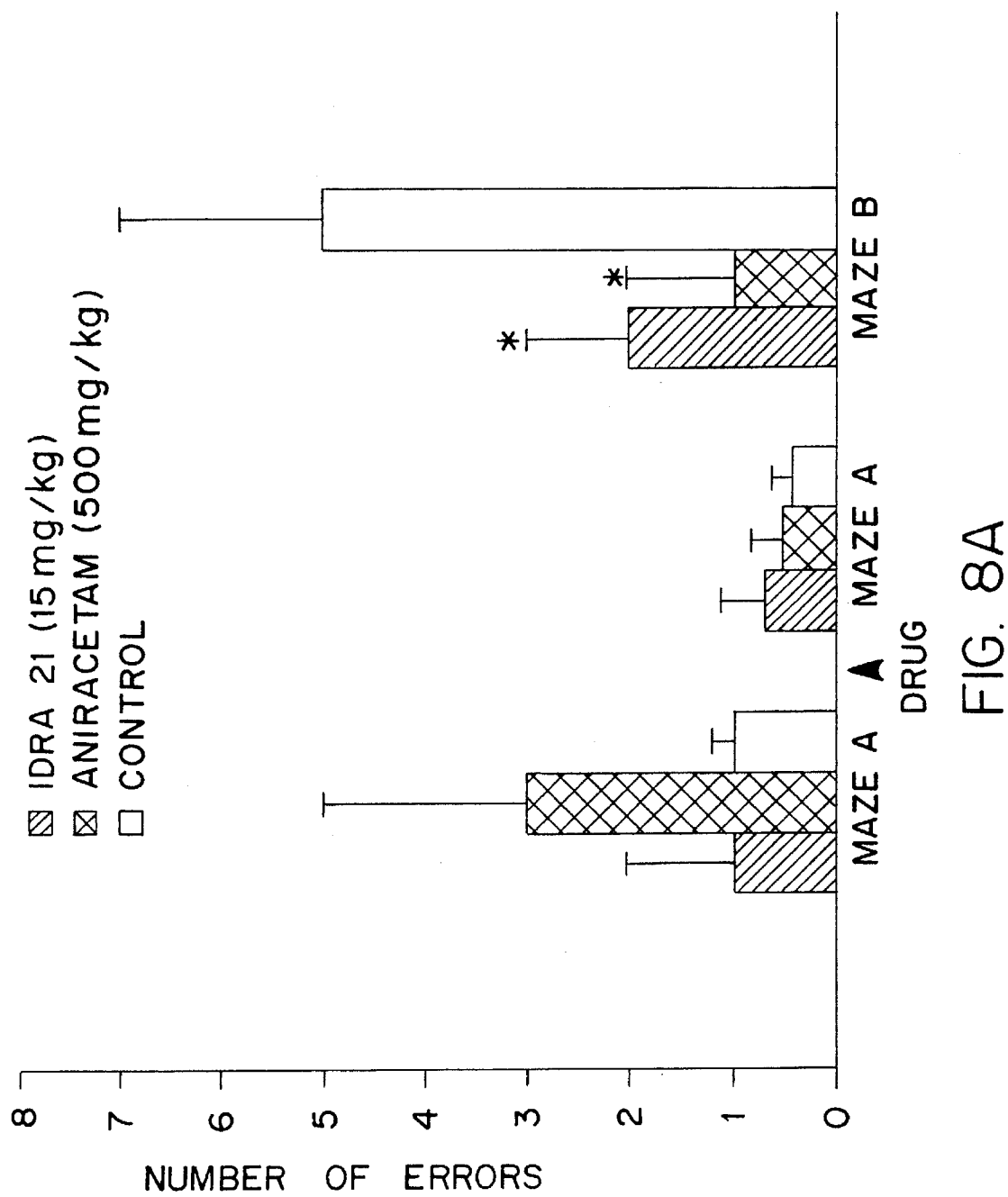
Figure 9A:
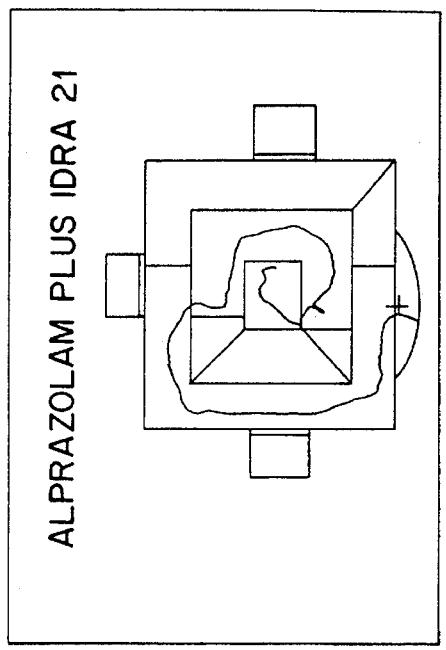
Figure 9A:
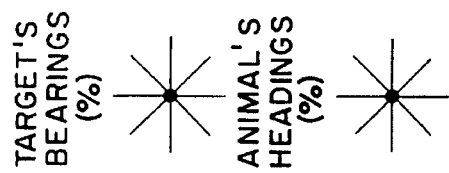
Figure 9B:
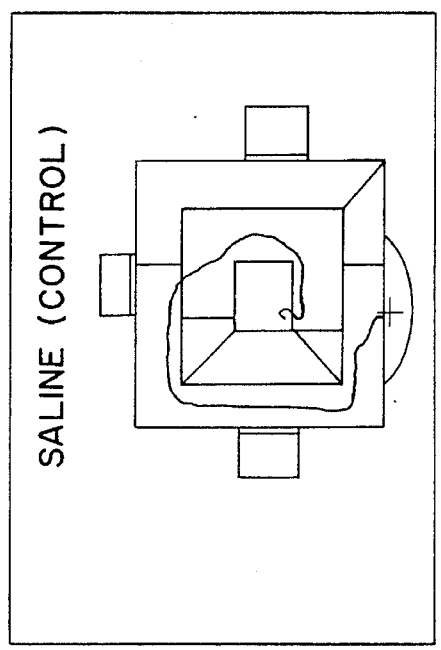
Figure 9B:
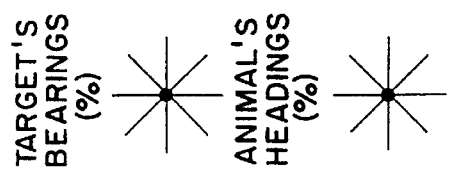
Figure 9C:
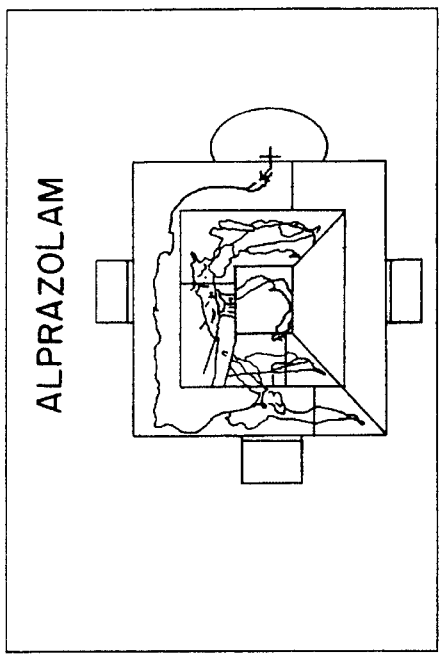
Figure 9C:
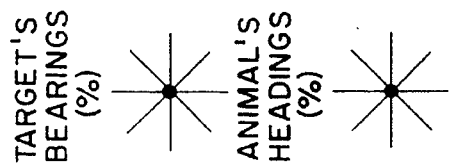
Figure 9D:
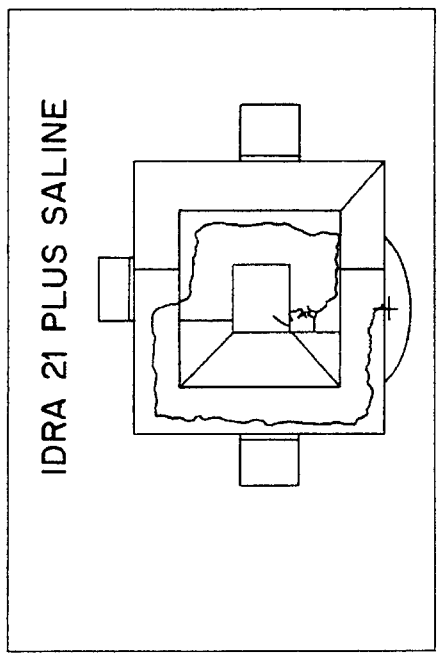
Figure 9D:
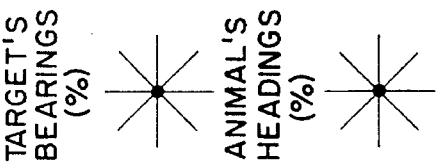

FIG. 8A shows that IDRA 21 and Aniracetam improve water performance in rats. Rats (male, 250 g) were trained once a day in maze A (See FIG. 8B forced maze) for 2 consecutive days. The day of the experiment, after a first exposure to maze A, IDRA 21 (15 mg/kg) Aniracetam (500 mg/kg) or vehicle (cont) were administered per oral gavage and 30 min later the animals were exposed once again to Maze A. After 30 min of interatrial rest, rats were exposed to Maze B (see FIG. 8C open maze).

Each bar represents the mean±SE of at least 5 rats. *P<0.05 when the control group is compared with IDRA 21 or the Aniracetam treated group.

Figure 7:
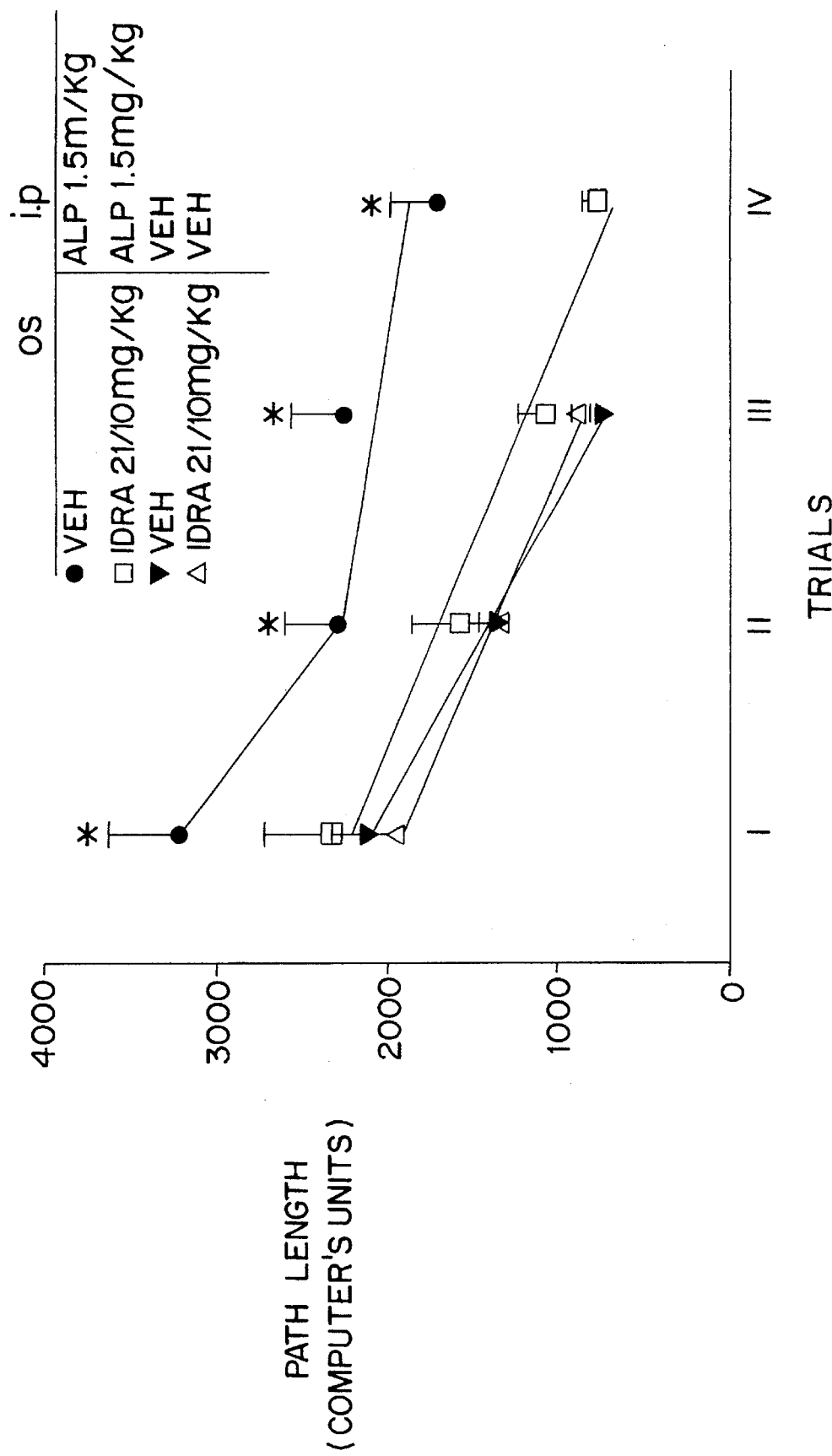
FIG. 7 shows that IDRA 21 attenuates the learning disruptive effect of Alprazolam (ALP) in the water maze test. Rats (male 250 g b.w.) were trained two days, once a day, in maze A (See insert A). The day of the experiment, rats received IDRA 21 (10 mg/kg) or water (VEH) via oral lavage. 30 min later ALP (1.5 mg/kg) or saline (VEH) were injected intraperitoneally (i.p.) in either IDRA 21- or water-treated rats. Rats were exposed to a new maze configuration (Maze B) in 4 successive trials 15, 30, 45, and 60 min after the i.p. injections.

FIGS. 9A, 9B, 9C and 9D show representative computer prints of the path length of the third trial of FIG. 7. Chromotrack, San Diego Instruments, San Diego, Calif.

Figure 10:
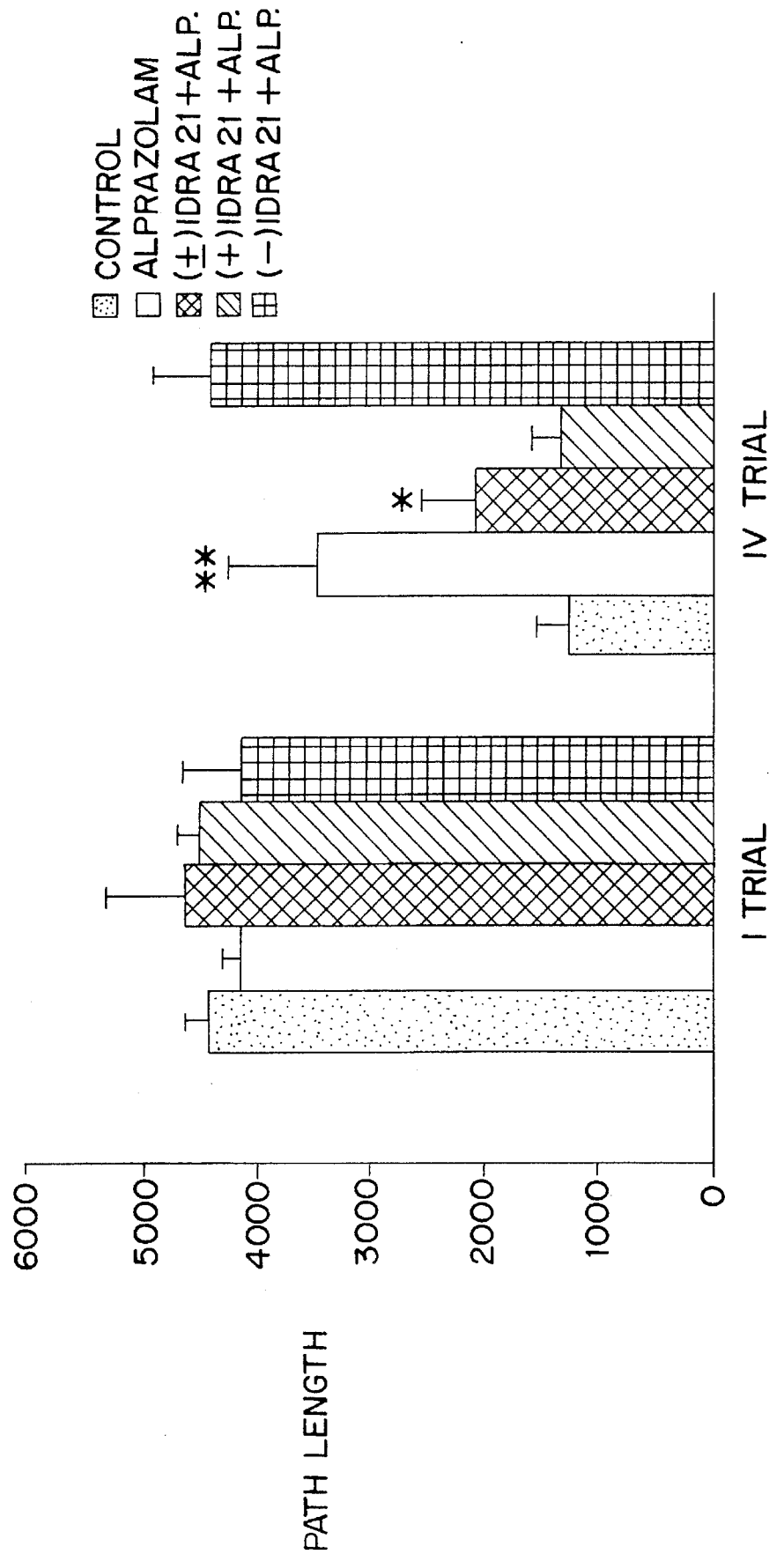

FIG. 10, shows that (+) IDRA 21 is more potent that (±) IDRA 21 and (−) IDRA 21 is antagonizing the Alprazolam-induced deficit in rats. The conditions are the same as those described in FIG. 10. IDRA 21 was administered per oral lavage in doses of 5 mg/kg. **P<0.01; *P0.05 when compared to controls. Each bar is the mean±SE of 5 rats.

DETAILED DESCRIPTION OF THE INVENTION

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The contents of each of the references cited herein are herein incorporated by reference in their entirety.

In the above definition of the (+) enantiomer according to the present invention, the lower alkyl group defined with respect to $R^3$ is a straight-chain or branched alkyl group having 1 to 8 carbon atoms and examples thereof include methyl, ethyl, propyl, isopropyl, butyl, isobutyl, sec-butyl, tert-butyl, pentyl(amyl), isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl groups.

The $C_2$–$C_8$ alkenyl group defined with respect to $R^3$ is a straight or branched chain alkenyl group having 2 to 8 carbon atoms having at least one double bond. Examples thereof include —CH=$CH_2$, —CH=$CHCH_3$, —$CH_2$CH=$CH_2$, —C($CH_3$)=$CH_2$, —CH($CH_2$)$_5$CH=$CH_2$, —CH=CH—CH=$CH_2$, —CH=CH—CH—CH—$CH_3$, —C(CH)=CH, —CH($CH_3$)CH=$CH_2$, —C($C_2H_5$)=CHCH($CH_3$)CH=$CH_2$, —C(CH)$_3$=CHCH($C_2H_5$)—CH=$CH_2$, and —CH=C($CH_3$)—$CH_2$—CH=C($CH_3$)$CH_3$.

The $C_2$–$C_8$ alkynyl group defined with respect to $R^3$ is a straight or branched chain alkynyl group having at least one triple bond. Examples include —CH≡CH, —C≡C—$CH_3$, —C≡C—($CH_2$)$_m$—$CH_3$ wherein m is 1–5, —$CH_2$—C≡CH, —$CH_2$—C≡C—$CH_3$, and —$CH_2$—C≡C(—$CH_2$)$_n$—$CH_3$ wherein n is 1–4.

The substituted $C_1$–$C_4$ alkoxy group for $R^3$ is derived from the respective above-mentioned lower alkyl groups and preferable examples thereof include methoxy, ethoxy and n-propoxy, isopropoxy.

The substituted $C_1$–$C_4$ thioalkyl group for $R^3$ is one derived from the above-mentioned alkyl groups having 1 to 4 carbon atoms and preferable examples include —S—$CH_3$, —S—$CH_2$—$CH_3$ and S—$CH_2CH_2CH_3$.

The halogen atoms defined with respect to $R^1$ and $R^2$ and substituted $R^3$ groups is chlorine, bromine, or fluorine.

The $C_3$–$C_6$ cycloalkyl group defined with respect to $R^3$ includes cyclopropyl, cyclobutyl, cyclopentyl and cyclohexyl groups.

The $C_3$–$C_6$ cycloakenyl group defined with respect to $R^3$ includes the above-mentioned $C_3$–$C_6$ cycloalkyl rings which include one or two double bonds.

The $C_6$–$C_8$ bicycloalkyl group for $R^3$ is an aliphatic saturated hydrocarbon group which is composed only of two rings with at least two bonds being jointly owned by the rings. A representative example of the bicycloalkyl group include:

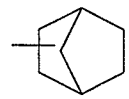

and a particular example is

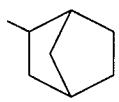

The $C_6$–$C_8$ bicycloalkenyl group is an aliphatic unsaturated hydrocarbon group which is composed of two rings with at least two bonds being jointly shared by each ring. Representative examples of bicycloalkenyl include:

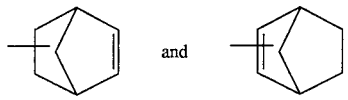

and a particular example is

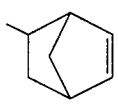

Included within the meaning of memory and learning disorders are:

learning disorders in children, such as impairment in communication, imaginative activity and associated features, as well as attention disorders in children;

learning and memory disorders resulting from trauma, stroke, epilepsy and neurodegenerative disorders;

learning and memory disorders associated with senile dementia such as Alzheimer's disease; and memory and learning disorders associated with alcohol intoxication and neurotoxoc agents such as PCP.

Memory disorders and learning disorders treatable according to the present method include those disorders which are the result of aging, trauma, stroke, and neurodegenerative disorders. Examples of neurodegenerative disorders include, but are not limited to those associated with alcohol intoxication, neurotoxic agents such as PCP, and Alzehiemer's disease.

Synthesis

The compounds which are useful in the present invention are prepared according to the following general reaction scheme

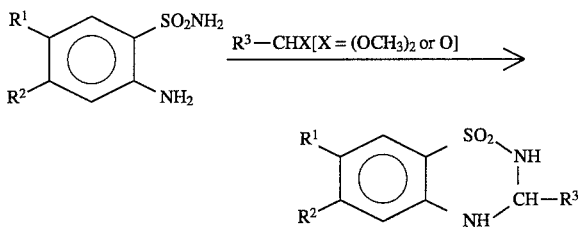

wherein $R^1$, $R^2$ and $R^3$ are defined above.

The use of appropriate organic solvents, temperature and time conditions for running the reaction are within the level of skill in t art.

The (+) enantiomer can be further separated by HPLC using the chiral selector (S)-(3,5-Dintrobenzoyl-2,6-Dimethylaniline covalently bound to a silica gel, and mobile phase.

The chemical structures of the various benzothiadiazide encompassed by the present invention are shown below (hereinafter referred to as IDRA compounds):

TABLE

| | $R^1$ | $R^2$ | $R^3$ |
|---|---|---|---|
| IDRA 21 | Cl | H | $-CH_3$ |
| | Cl | H | $-CH_2CH_3$ |
| | Cl | H | -n-propyl |
| | Cl | H | -isopropyl |
| | Cl | H | -n-butyl |
| | Cl | H | -iso-butyl |
| | Cl | H | -sec-butyl |
| | Cl | H | -n-pentyl |
| | Cl | H | -n-hexyl |
| | Cl | H | $-CH=CH_2$ |
| | Cl | H | $-CH_2Cl$ |
| | Cl | H | $-CH_2CH_2Cl$ |
| | Cl | H | $-CH_2NH_2$ |
| | Cl | H | $-CH_2-O-CH_3$ |
| | Cl | H | $-CH_2CH_2-O-CH_3$ |
| | Cl | H | $-CH_2CH_2-O-CH_2CH_3$ |
| | Cl | H | $-CH_2-S-CH_3$ |
| | Cl | H | -cyclohexyl |
| | Cl | H | 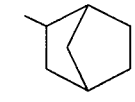 |
| IDRA 23 | Cl | H | 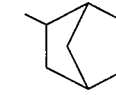 |
| IDRA 22 | $SO_2NH_2$ | Cl | $-CH_3$ |
| IDRA 20 | H | Cl | $-CH_3$ |
| | H | Cl | $-CH_2CH_3$ |
| | H | Cl | -n-propyl |
| | H | Cl | -iso-propyl |
| | H | Cl | -n-butyl |
| | H | Cl | -iso-butyl |
| | H | Cl | -sec-butyl |
| | H | Cl | -n-pentyl |
| | H | Cl | -n-hexyl |
| | H | Cl | $-CH=CH_2$ |
| | H | Cl | $-CH_2Cl$ |
| | H | Cl | $-CH_2CH_2Cl$ |
| | H | Cl | $-CH_2NH_2$ |
| | H | Cl | $-CH_2-O-CH_3$ |
| | H | Cl | $-CH_2CH_2-O-CH_3$ |
| | H | Cl | $-CH_2CH_2-O-CH_2CH_3$ |
| | H | Cl | $-CH_2-S-CH_3$ |
| | H | Cl | -cyclohexyl |
| | H | Cl | 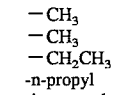 |
| | H | Cl | 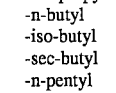 |

6-chloro-3-methyl (IDRA 20), 7-chloro-3-methyl (IDRA21) and 6-chloro-7-sulfonyl-3-methyl (IDRA22) and 6-chloro-3-bicyclo[2.2.1]-hept-2-ene (IDRA 23)-3,4 -dihydro-2H 1,2,4-benzothiadiazine S-S dioxide were prepared by minor modifications of the methods of Werner, L. M., Halamandans, A., Ricca, S., Dorfman, L., and DeStevens, G. (1960) J. Am. Chem. Soc., 82, 1161– 1166; Topliss, J. G., Sherlock, M. H., Reimann, H., Konzelman, L. M., Shapiro, E. P., Pettersen, B. W., Schneider, H., and Sperber, N. (1963) J. Med. Chem. 6, 122–127; Suzue, S. and Hayashi, S., (1962) Yakugaku Zasshi, 82, 1192 in Chem. Abstr. (1963) 38, 5689c.; Todor, P., Gyorgy, L. and Antal, G., (1969) Hung 155,544 (ClC 07d), 25 Jan 1969, Appt 21 Dec 1966 in Chem Abstr. 70, 115187d (1969), respectively, and as follows: The corresponding 2-amino-benzenesulfonamides (0.01 mol)

were heated with acetaldehyde (0.1 mol) in a sealed tube at 60° C. for four hours. The crude products are purified by crystallization from acetone and petroleum ether, in yields of 87%, 88% and 89%, for IDRA 20, 21 and 22, respectively. IR spectra and chemical analyses are consistent with the assigned structures.

Melting points were the same for compounds synthesized by different methods (13,14).

Also contemplated as useful in the present invention are IDRA derivatives in which the chlorine at positions $R^1$ and $R^2$ are substituted with fluorine or bromine, as well as straight and branched chain $C_1-C_8$ alkyl groups at the $R^3$ position of IDRA 20–23 which can be prepared according to the above-described procedures Werner et al, Topliss et al, Suzue et al and Todor et al by employing the appropriate substituent 2-amino-benzenesulfonamide.

Separation of the (+) and (−) enantiomers

The IDRA compounds are chiral with a stereogenic center on the ring thiadiazine at the $R^-$ position where $R^3$ is bound to the ring. It has been discovered that the potency and efficacy are dependent upon the intrinsic properties of (+) enantiomer.

The separation of the enantiomers of the racemic IDRA compound, including IDRA 21, was carried out on a homemade chiral stationary phase.

The chiral stationary phase (CSP) is prepared by covalently bonding the chiral selector (CS) to silica gel (5 micron, 100 A, Regis, Morton Grove, Ill. 60053).

Preparation of the chiral selector racemic

The CS is prepared by acylating allylglycine (DL-2-Amino-4-pentenoic acid, Aldrich Chemical Co., Inc.) with 3,5-Dinitrobenzoyl chloride according to the procedure of C. Welch and W. Pirkle, Journal of Chromatography, 609 (1992) 89–101. The acylating reagent is prepared by refluxing under nitrogen 3,5-Dinitrobenzoic acid (Aldrich) and thionyl chloride (Aldrich) in dry methylene chloride for 24 h. After the solvent and the excess thionyl chloride are distilled off, 3,5-Dinitrobenzoyl chloride is recrystallized from hexane/methylene chloride to afford a yellow solid (95% yield), m.p. 69°–70° C. The product of the acylation, DL-N-(3,5-Dinitrobenzoyl)-2-amino-4-pentenioc acid, is reacted with 2,6-Dimethylaniline using the coupling reagent EEDQ (2-ethoxy-1-ethoxycarbonyl-1,2-dihydroquinoline, Aldrich Chemical Co.) according to a procedure described in M. Bodanszky and A. Bodanszky, The Practice of Peptide Synthesis, Springer-Verlag, New York, 1984, p. 148.

Preparative resolution of the enantiomers of DL-N-(3,5-Dinitrobenzoyl)-2-amino-4-pentenoic acid-2,6-dimethylanilide The enantiomers are separated by preparative chromatography on a 2.5×75 cm column packed with (S)-N-(1-naphthyl)leucine covalently bonded to 40 micron silica gel. The mobile phase is 20% 2-propanol in hexane. The initially eluting enantiomer is assigned an (R) absolute configuration based on mechanistic considerations. Each enantiomer is obtained as a white solid. The enantiomeric purity of both enantiomers is greater than 99% as determined by analytical HPLC. Each enantiomer has a $^1$H NMR spectrum identical to that of the racemate.

Preparation of the chiral stationary X phase

The second eluting enantiomer, (S)-(−)-N-(3,5-Dinitrobenzoyl)-2-amino-4-pentenoicacid-2,6-dimethylanilide is converted to an organosilane and bonded covalently to silica gel as described by Pirkle et al., Journal of Organic Chemistry, 57, 1992, 3854–3860.

The CSP is packed into a 250×4.6 mm stainless steel HPLC column as a methanol slurry using a conventional down-flow packing technique. The CSP is endcapped by passing a solution of 4 mL hexamethyldisilazane in 70 mL of methylene chloride through the column at a flow rate of 1 mL/min. Elemental analysis of the packing material showed a column loading of 0.1957 mmol/g based on carbon and 0.1160 mmol/g based on nitrogen. The void volume of the column is determined with 1,3,5-tri-tert-butylbenzene (W. H. Pirkle, C. J. Welch, Journal of Liquid Chromatography, 14, 1, 1991).

HPLC enantiomeric resolution of (±) IDRA-21.

The mobile phase employed is: hexane/2-propanol/methylene chloride/acetonitride (100:2:10:0.1; flow rate 2 ml/mm; UV 254 mm, 10 μg of racemate injected; retention time 37.5 min and 44.3 min, respectively; α=1.2.

Figure 1:
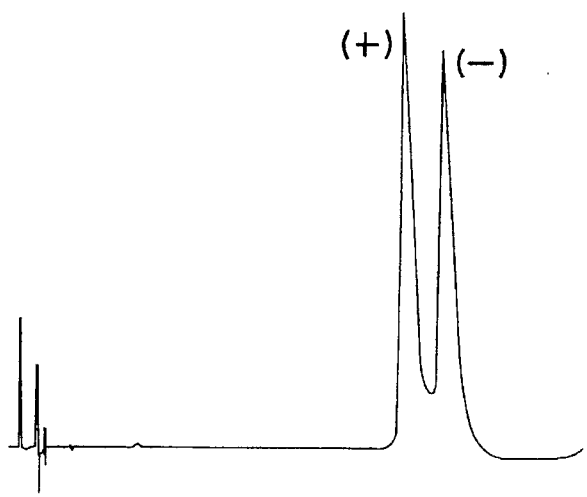
FIG. 1 shows the Chiral High-performance liquid chromatographic resolution of (±) IDRA 21. Mobile phase: hexane/2-propanol/methylene chloride/acetonitrile (100:2:10:0.1); flow rate 2 ml/mm; UV 254 nm, 10 μg of racemate injected; retention time 37.5 min and 44.3 min, respectively; α=1.2.

As seen in FIG. 1, the first peak eluted from the column is the (+) enantiomer, and the second is the (−) enantiomer. The specific rotation of the second peak is determined to be $[\alpha]^{24} = -104°$ in ethanol (Perkin-Elmer Polarimeter 241 MC).

EXAMPLE 1

Electrophysiological Experiments: Positive Allosteric Action of the Invention Compounds on APMA/Kainate Receptors A) Materials and Methods Tissue Preparation.

Young rats (12–16 days old) were decapitated and the brains quickly removed and placed in ice-cold Ringer solution. Thin slices of hippocampus (250 μm) were then cut with a vibratome slicer (Lancer, St. Louis, Mo.) and kept in Ringer solution at 37° C. until use. The experiments were carried out at room temperature with the slice totally submerged in a 1 ml volume recording chamber and under continuous perfusion with Ringer solution at a rate of 6 ml/min using an upright Hoffman modulation contrast microscope (Carl Zeiss, Germany) equipped with a 40×water immersion objective.

Media and drug application. The external Ringer solution contained (in mM): NaCl 120; KCl 3.1; $CaCl_2$ 2; $MgCl_2$ 1; $KH_2PO_4$ 1; $NaHCO_3$ 26; glucose 2.7; and it was continuously bubbled with 95% $O_2$ and 5% $CO_2$. Patch pipettes were filled with a solution containing (in mM): K-gluconate 140; $MgCl_2$ 1; ATP.Mg 2; EGTA 0.5; HEPES-KOH 10, pH 7.2. All the drugs under investigation were applied through the recording chamber perfusion system via parallel inputs having a common entry into the chamber. Agonist application was attained using two different systems that allowed a slow or a rapid solution change. Slow solution changes were used during recordings in whole-cell configuration and were obtained by exchanging the solution of the recording chamber within a few seconds. Fast solution changes were obtained with the use of the Y-shaped tubing method that allows complete exchange of solution in less than 10 ms, and is described in detail by Murase et al. (1989).

Briefly, a polyethylene tubing (1 mm i.d.) is bent in a U-shaped, and another fine polyethylene tubing (50 μi.d.) and 10 mm length) is inserted into a small hole in the U-tubing making the tip of the Y-tubing. Solutions are fed to the Y-tubing by gravity, and negative pressure facilitates exchange of the solution. The tip of the Y-tubing is positioned 100 μm from the cell investigated, and upon opening and closing of a valve that controls the negative pressure, it was possible to respectively change rapidly and apply a number of different test solutions. This method was used to apply agonists to excised outside-out membrane patches.

More rapid drug applications were used to apply agonists to excised outside-out membrane patches, and were obtained through a double-barrelled pipette positioned close to the recording pipette containing the membrane patch. One barrel was filled with Ringer control solution and the other with Ringer solution containing 1 mM glutamate or kainate. The agonist was applied for a period of 150 ms and the time necessary for a complete exchange of the solution was less than 1 ms as measured at the opening of a patch pipette containing different dilutions of the drugs under study. When glutamate was used as the receptor agonist, the solution contained 5 μM dizolcipine (MK-801) to block the NMDA receptor channels.

IDRA compounds (see above for structures) were first dissolved in 50 μl of DMSO, then 50 ml of 1N NaOH and water (sufficient to reach a volume of 1 ml and a concentration of 10 mM). The final concentration was reached diluting the stock solution with Ringer solution.

Electrophysiological Recordings.

Ionic currents in whole-cell configuration and outside-out excised membrane patches were monitored using the patch clamp technique (15). Currents were recorded with a List EPC7 amplifier (Darmstad, Germany), filtered at 2 kH (8 pole, lowpass Bessel, Frequency Devices, Haverhill, Mass.) continuously displayed on an oscilloscope and stored on a magnetic tape (Racal Recorders, Southampton, England) for subsequent analysis.

Data Analysis

Dose-response hoottopic drugs on glutamate activated currents.

Dose-response studies were performed with the Y-tubing system, and analyzed with sigmoid interpolation (Graphpad Academic Press).

EPSC and glutamate activated currents.

Traces were filtered at 3 KHz (−3 dB, 8-pole, lowpass Bessel filter, Frequency Devices), and stored in an LSI 11/73 computer (INDEC System, Sunnyvale, Calif.) after digitization (10 KHz) with a Data Translation analog to digital converter. Decay time constants of EPSC and glutamate-activated currents were determined from exponential fitting with the 11/73 system by using an entirely automated least-squares procedures (see Vicini and Schuetze, 1985, for further details). This method uses a Simplex algorithm (Cacecci and Cacheris, 1984) to fit the data to either a single or double exponential equation of the form $I(t)=I_f \exp(-t/\tau_f)+I_s \exp(-t/\tau_s)$, where $I_f$ and $I_s$ are the amplitudes of the sIPSC fast and slow components, and $\tau_f$ and $\tau_s$ are their respective decay time constants. Peak amplitudes were measured at the absolute maximum of the currents, taking into account the noise of the baseline and noise around the peak. Rise times were measured as the time elapsed from 20 to 80% of the peak amplitude of the response.

Results are expressed as means±S.E.M.

B) Results

Nootropic drugs and AMPA receptor electrophysiology.

The action diazoxide and the IDRA analogues were tested on the desensitization of AMPA receptors located on CA1 pyramidal neuronal membranes in rat hippocampal slices. In order to evaluate whether the compounds under study increase the intensity of currents generated by the activation of non-NMDA receptors, these receptors were activated with glutamate in the presence of 5 μM MK-801 to block completely the ionic current elicited by glutamate acting on the NMDA receptor channels present in CA1 pyramidal neurons. Three distinct methods of drug application were employed: 1) slow bath perfusion of agonist and drugs while recording in whole-cell mode (onset 30s); ii) fast application to outside-out patches of a fixed concentration of agonist with a double barrel pipette (onset<1 ms) in the presence and the absence of drugs; iii) fast perfusion (onset<6 ms) of increasing concentrations of agonist and drugs applied with the Y-tubing device to outside-out patches excised from neurons in brain slices and to voltage-clamped neurons in primary culture.

i) Slow Perfusion Studies

Figure 2:
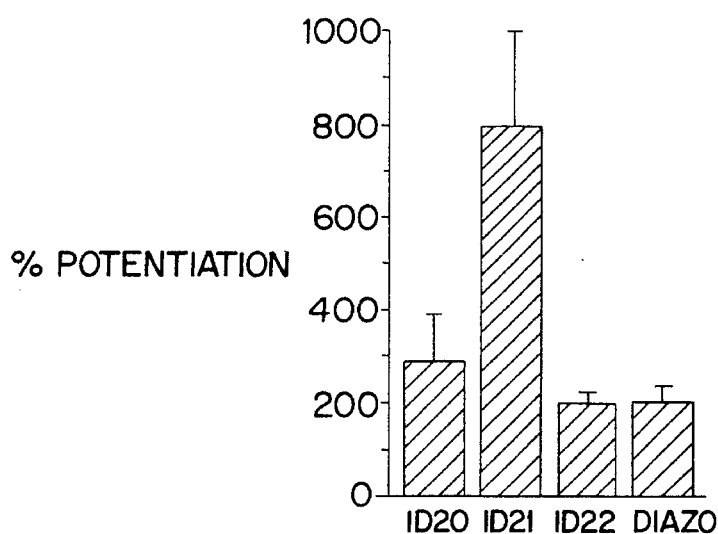
FIG. 2 shows the potentiation of glutamate-activated current by several IDRA compounds (1 mM). The concentration of 1-glutamate was 50 μm and the neurons were studied at a holding potential of −60 mV.

IDRA 20–23 were tested at a concentration of 1 mM on the ionic currents elicited by 50 μM glutamate in the presence of MK-801 (5 μm), and their ability to increase glutamate-elicited currents was compared to that of diazoxide. FIG. 2, shows the glutamate potentiation elicited by those IDRA compounds that were found to be capable of increasing the intensity of glutamate-elicited currents. The most efficacious (1 mM) derivative was IDRA21, which elicited a potentiation of 797±220% (n=4 cells), followed by IDRA 20 with a potentiation of 292±100% (n=4 cells) (FIG. 2). The other compounds that were active, including IDRA 23, were either equally or less efficacious than diazoxide.

In comparison, IDRA 21 and diazoxide elicited a dose-dependent potentiation; however, it was not possible to estimate their maximal efficacy since these compounds failed to reach maximal efficacy at 1 mM, the maximal dose that could be tested in the absence of a direct effect of the vehicle. IDRA 21 (10 μm) increased the current by 65±6.9% (mean±SE, N=4 cells), and at 100 μM, it potentiated the current by 109±30% (mean± SE, N=4 cells), while diazoxide at 100 μM was still inactive, and at 500 μM, the current was potentiated by 152±0.2% (mean±SE, N=4 cells). However, IDRA 21 (1 mM) was 4-fold more efficacious than diazoxide (797±200%; n=5 cells) (FIG. 2).

ii) Fast application studies with double barrel pipette.

To better understand the mechanism of action of IDRA 21, its action AMPA receptor desensitization using fast agonist application to outside-out membrane patches was investigated. The fast application of 1 mM glutamate in the presence of MK-801 (5 μM) in outside-out membrane patches excised from the CA1 hippocampal pyramidal neurons elicited a fast transient current followed by a sustained plateau. To verify that the response was elicited by an exclusive action of glutamate on the non-NMDA receptor and that there was not a contribution to the plateau response of different subtypes of AMPA-kainate receptors, 5 μM NBQX (1,2,3,4 -tetrahydroxy-6-nitro-2,3-dioxo-benzo-[f] quinoxaline-7-sulfonamide), a competitive antagonist of the non-NMDA receptors, was applied, and both transient peak currents and sustained plateau currents were completely blocked.

Figure 3:
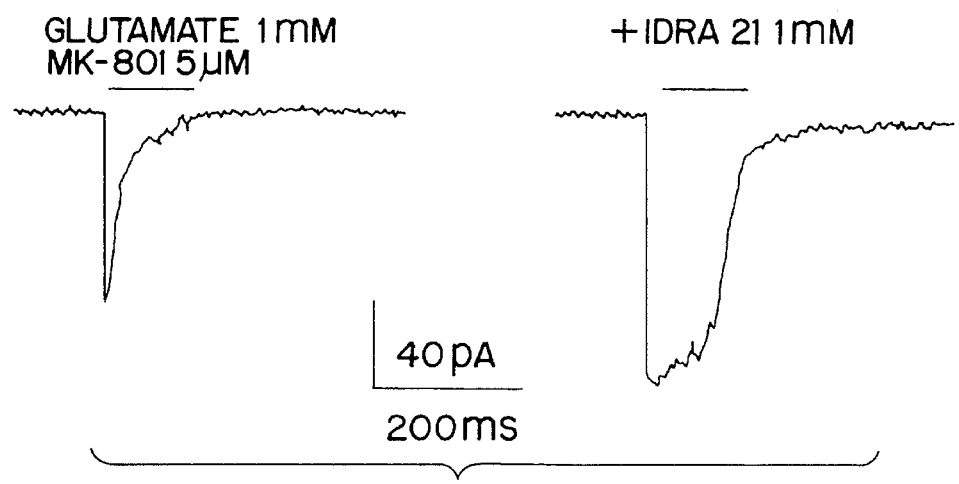
FIG. 3 shows that the desensitization of the current activated by 1 mM glutamate in the presence of 5 μM MK-801 in an outside-out patch is removed by 1 mM IDRA 21 Double Barrel application. Holding potential—60 mV.

IDRA 21 was then tested on the current activated by the fast application of 1 μM glutainate and 5 mM MK-801 to excised outside-out patches. Similarly to cyclothiazide (but at a higher dose), 1 mM IDRA 21 completely removed the desensitization induced by glutamate in 4 of 5 patches tested (FIG. 3).

iii) Fast application studies with Y-tubing.

Figure 4A:
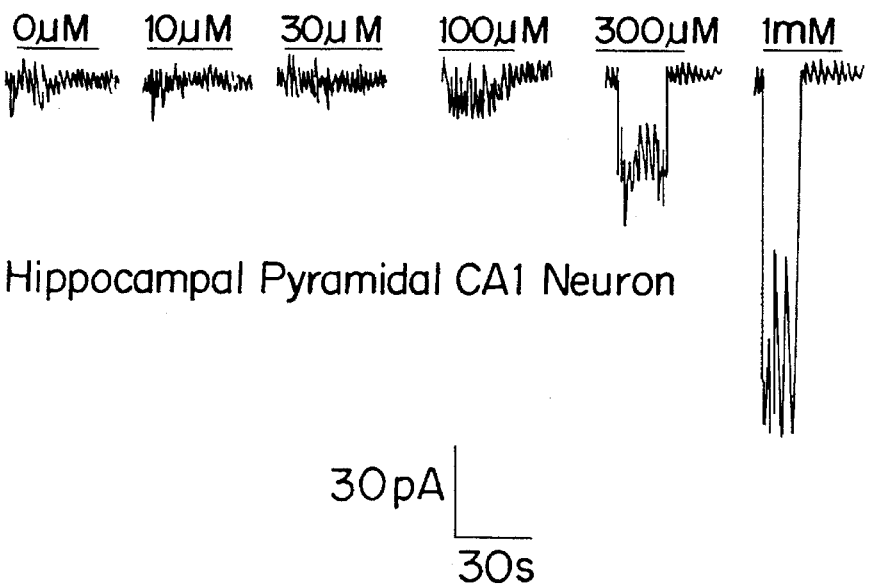
FIGS. 4A and 4B shows that the desensitization of the current activated by 100 μM glutamate in the presence of 5 μM MK-801 in outside-out patches from two distinct CA1 pyramidal neurons is decreased by increasing doses of IDRA 21. Y tubing application. Holding potential −60 mV.
Figure 4B:
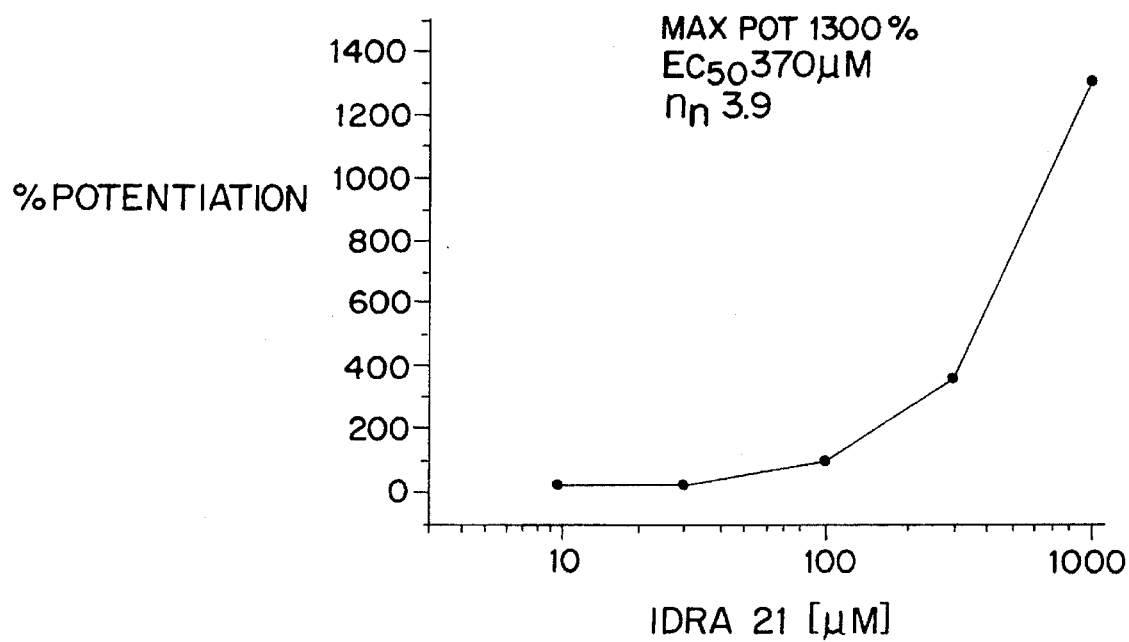
Figure 5A:
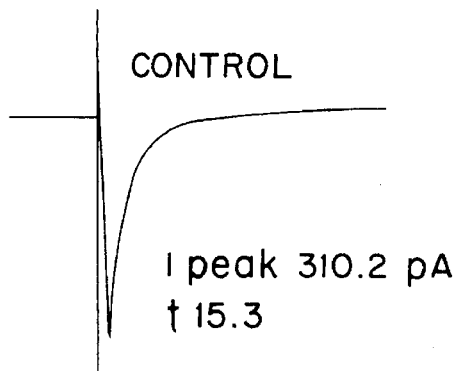
FIGS. 5A, 5B, 5C and 5D show EPSCs with superimposed fitting of the decay phase with a single exponential curve in the presence and the absence of diazoxide and IDRA 21 (both at 1 mM). Holding potential −60 mV.
Figure 5B:
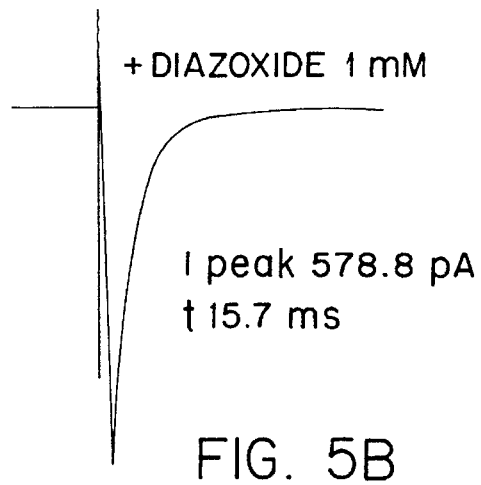
Figure 5C:
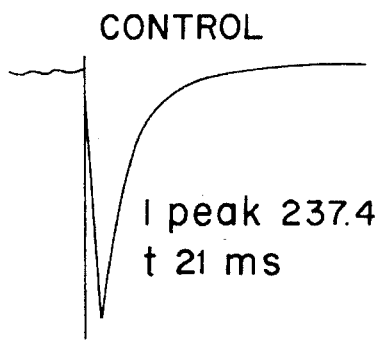
Figure 5D:
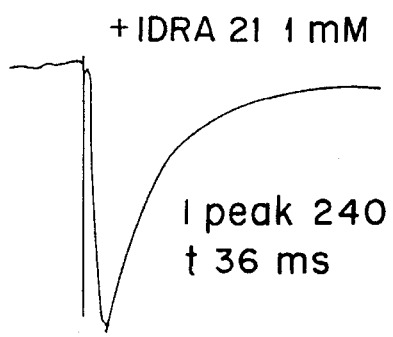

The action of ionotropic drugs on AMPA receptor stimulation in outside-out patches prepared from hippocampal slices and in neurons in culture patched clamped in the whole-cell mode administering the compounds with the Y-tubing device that allows the performance of dose-response studies was also tested. FIG. 4 shows the dose-response of IDRA 21 on 100 μM 1-glutamate in the presence of MK-801 (5 μM) to an outside-out patch excised from two distinct CA1 pyramidal hippocampal neurons.

Selectivity of nootropic drugs: electrophysiology.

Aniracetam, diazoxide, cyclothiazide and IDRA 21 were tested on the ionic current elicited by 20 μM kainate.

Diazoxide (1 mM), and 40 μM cyclothiazide increased the current. Conversely, aniracetam (1 mM) and IDRA 21 (1 mM) failed to potentiate the kainate-activated current which shows the selectivity for the AMPA receptor.
AMPA receptor subtypes in excitatory synapses of selected limbic circuits.

The action of nootropic drugs on the excitatory postsynaptic currents (EPSCs) elicited in CA1 pyramidal neurons in hippocampal slices was investigated by stimulation of the Schaffer collateral afferents. In FIG. 5, EPSCs are shown in the presence and in the absence of diazoxide and IDRA 21. IDRA 21 increased the delay time of the current generated by AMPA receptor stimulation with an efficacy 3 times larger than that of diazoxide.

EXAMPLE 2

Figure 6A:
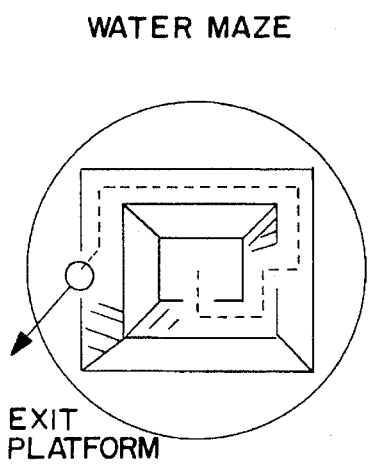
FIGS. 6A and 6B are diagrams illustrating maze A and maze B, respectively Shaded regions denote possibilities for errors.
Figure 6B:
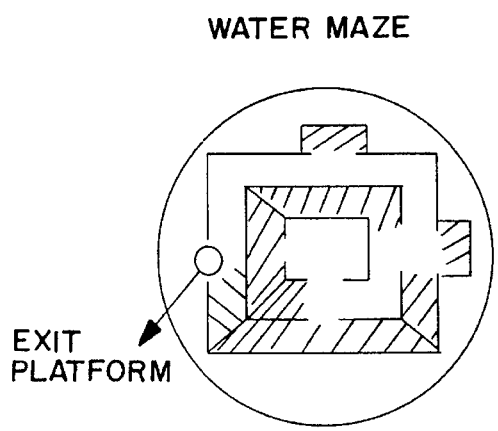

Nootropic Action of the Invention Compounds in Rats a) Materials and Methods
i) Water maze apparatus:
The water maze apparatus was adapted from Kant et al., (16), and consists of three concentric squares placed inside a 5 ft plastic pool (FIG. 6). The walls of the maze are 50 cm in height and are constructed from black opaque plastic to allow for tracking of the animal with an overhead camera. The alleys between the walls are 16 cm wide. In the center of each wall there is a removable doorway. The opening of doorways allows for the construction of mazes with an increasing number of potential error possibilities. (See diagram for Maze A and Maze B, FIG. 6). The maze is located in a room 10'× 15' at constant temperature (18° C.) adjacent to the vivarium. The room is illuminated with overhead lights which also serve as spatial cues. Additional spatial cues are provided by the position of the investigator and a number of small white x's placed within specific locations upon the walls of the maze. The maze is filled with water (18°)C. to a depth of 25 cm.
ii) Assessment of Drug Action on Learning and Retention
Seven days prior to drug studies, rats were tested in Maze A (forced maze) on two consecutive days. Pretesting with the "forced" maze enabled the assessment of the animals' general motor, sensory and motivational abilities, and facilitated the exclusion of those animals unable to meet pretesting criteria. Performance was assessed by determining either swim time, errors committed, or path length measured with a computerized recording device. Errors are defined as whole body entry into alleys not leading directly to the exit platform (i.e., shaded portions in FIG. 6). Rats were excluded from the study if their swim path length and/or number of errors were two standard deviations above the mean swim speed of the entire group. During the first two trials, the rats were placed into the center of the maze and given a maximum of 180 secs to find the "exit platform" located at the "finish" (FIG. 6). The time required, the number of errors, and the path length were recorded for each trial. Rats that failed to reach the platform in 180 secs were removed from the maze, returned to their cages and given a swim time of 180 secs. Rats meeting the criteria were randomly divided into groups. On the day of the experiment, a single trial was run (Maze A) in order to establish a baseline of performance. Following drug administration, the rats were again tested once on Maze A to establish a baseline of post-treatment performance. Following an additional interatrial interval of 30 min., the rats were tested on Maze B.

iii) Assessment of the Drug Action on Alprazolam-Disrupted Learning Behavior
In these experiments, rats were trained in Maze B 15, 30, 45 and 60 min. after drug injection. In this test paradigm, rats learn the task in the second or third trial, whereas alprazolam-treated rats failed to do so (See FIG. 7).

Results a) Effect of IDRA 21 on Learning and Retention
As shown in FIG. 8, IDRA 21 (15 mg/kg os) significantly improves the performance of rats, reducing the number of errors and the time interval in accomplishing the task in Maze B. Similar effects were obtained when 400 mg/kg os of aniracetam were administered.
IDRA 21 given in a dose of 0.2 μmol icv was shown to be at least as efficacious as aniracetam (1.8 μmol icv) in improving the performance of trained rats in the water maze test.
b) Effect of IDRA 21 on the Amnesic Effect of Alprazolam
As shown in FIG. 7, rats treated 15 min before the test intraperitoneally with 1.5 mg/kg of alprazolam (a positive allosteric modulator of $GABA_A$ receptors) fail to learn how to reach the platform in the water Maze B. This is expected since GABAmimetic drugs and some potent benzodiazepine ligands are known to disrupt learning and memory processes in man (17). The pretreatment with IDRA 21 (10 mg/kg os, 30 min) reduces the amnesic effect of alprazolam (FIG. 7 and FIG. 9). This is probably a functional antagonistic action against the learning and memory deficit elicited by an increase in GABAergic synaptic strength. Interestingly, diazoxide and chlorothiazide, in doses equimolar to IDRA 21, were inactive.
c) The (+) IDRA 21 enantiomer is the active species in antagonizing the amnesic effect of alprazolam at the dose tested
FIG. 10 shows that (+) IDRA 21 is the stereoisomer active in preventing alprazolam-induced amnesia in rats. At an oral dose of 5 mg/kg, (+) IDRA 21 is significantly more potent than (±) IDRA; (−) IDRA is inactive.
In summary of the above-described results, electrophysiologically, IDRA 21 produces a reduction in the desensitization of AMPA/Kainate receptors.
IDRA 21 produces a response 3 times larger than diaxozide and one order of magnitude larger than that of aniracetam. Moreover, while cyclothiazide and diazoxide potently potentiated kainate responses for all the doses that decreased AMPA desensitization, IDRA 21 and aniracetam inhibited AMPA desensitization in doses that failed to affect kainate responses.
When administered in animals, IDRA 21 in the racemic form is at least an order of magnitude more potent than aniracetam in potentiating learning and enhancing cognitive performance both in naive rats and in rats with disrupted learning behavior (i.e., with alprazolam).
When resolved into enantiomers, the (+) IDRA 21 is biologically active, whereas the (−) IDRA 21 is inactive. Thus, (+) IDRA 21 is useful for the treatment of learning and memory deficits.
Preliminary electrophysiological and biochemical radiolabeled binding studies indicate that (+) IDRA 21 fails to act directly on $GABA_A$ receptors; presumably (+) IDRA 21 antagonizes the disruptive action of alprazolam by increasing the excitatory synaptic strength, of depolarizing synapses and thereby counteracting the neuronal hyperpolarization elicited by the potentiation of GABAergic transmission elicited by alprazolam. The effect of (+) IDRA 21 occurs for doses which fail to affect the gross animal behavior (no changes in exploratory behavior, stereotypy, ataxia, posture, etc.). Most important for the present invention is the fact that diazoxide and cyclothiazide administered to rats in amounts equimolar to (+) IDRA 21 are unable to antagonize alprazolam-induced impairment of learning behavior. In vitro electrophysiological experiments, diazoxide and cyclothiazide are at least as efficacious as (+) IDRA 21 in increasing excitatory synaptic strength in CAI pyramidal neurons. The lack of the effect of diaxozide and cyclothiazide in the in vivo experiments indicates that presumably the latter two drugs fail to enter the brain. Thus, (+) IDRA 21, when compared with other known drugs that increase excitatory amino acid synaptic strength, possesses the unique feature that in relatively small doses, it can be administered to animals and can be taken up by the brain in a sufficient quantity to produce learning and memory enhancing effects. This effect is dose-dependent, and lasts longer than 1 hr. Both characteristics suggest the clinical use of the IDRA compounds as nootropic agents.

The potent action of (+) IDRA 21 against alprazolam-induced impairment of learning behavior in rats emphasizes the importance of the use of allosteric modulators of transmitter action in preclinical drug development. The use of allosteric modulators of a primary transmitter system is particularly advantageous in therapy (18) because these drugs fail to disrupt the intermittence of synaptic transmission while increasing the strength of the synaptic function. Thus, these drugs provide a fine tuning of the synaptic activity by only upregulating its strength. In the case of glutamate and of drugs that are capable of increasing glutamatergic synaptic strength, the use of allosteric modulators rather than that of isosteric agonists acquires particular therapeutic significance. In fact, glutamate released intermittently in small quanta in the synaptic cleft, acting on ionotropic and metabotropic receptors, possesses physiological excitatory and trophic effects on the post-synaptic neurons, whereas glutamate released in large amounts and for protracted periods of time acting paroxistically at the ionotropic receptors produces excitotoxicity and neuronal death.

Isosteric agonists of AMPA/kainate receptors endowed with high intrinsic efficacy (i.e., kainate and AMPA) not only summate their action with that of the natural transmitter glutamate, but because they continually stimulate the receptor, induce neurotoxicity. In contrast, positive allosteric modulators of the AMPA/kainate receptors such as (+) IDRA 21, by reducing the rate of receptor desensitization, potentiate the excitatory synaptic strength by facilitating the action of the transmitter. They act without disrupting intermittency of glutamate release from the presynaptic sites or its reuptake and degradation in neighboring neurons and glial cells, and without increasing the action of glutamate at metabotropic receptors. Positive allosteric modulators are not only devoid of neurotoxicity, but since synaptically released glutamate may be neurotrophic, they may also facilitate this action of glutamate.

There are two types of memory which can be modified pharmacologically: a) long-term memory, reference memory or constant memory (19), which is characterized by the ability to learn or retain a constant set of relationships among events; and b) short-term memory, working memory or unique memory, which is relevant to specific events in relationship within a given time context (19,20).

Short-term memory performance is useful in evaluating the profile of condition-enhancing drugs because short-term memory impairment is an important consequence of aging, brain injury and exposure to drugs and toxicants (21,22). The present studies with (+) IDRA 21 emphasize the effect of these memory enhancing drugs on short-term memory performance in rats. With the exception of aniracetam and its congeners—which are very weak and short-lasting agents—relatively few drugs have been shown to facilitate short-term memory performance.

The present IDRA compounds are useful for enhancing both short-term memory, long-term memory, and cognitive performance in man. Preliminary experiments in Pacata monkeys with (+) IDRA 21 indicate that this drug is very potent in enhancing working memory. As a result, the compounds of the present invention are useful as therapeutic agents in memory impairment, e.g., due to toxicant exposure, brain injury, epilepsy, mental retardation in children and senile dementia, including Alzheimer's disease.

Pharmaceutical Compositions

The compounds may be formulated into pharmaceutical compositions by combination with appropriate, pharmaceutically acceptable carriers or diluents, and may be formulated into preparations in solid, semi-solid, liquid or gaseous forms such as tablets, capsules, powders, granules, ointments, solutions, suppositories, injections, inhalants, and aerosols in the usual ways for their respective route of administration.

The compounds can be administered alone, in combination with each other, or they can be used in combination with other memory or learning enhancing agents.

The following methods and excipients are merely exemplary and are in no way limiting.

In pharmaceutical dosage forms, the compounds may be administered in the form of their pharmaceutically acceptable salts, or they may also be used alone or in appropriate association, as well as in combination with other pharmaceutically active compounds.

In the dose of oral preparations, the compounds may be used alone or in combination with appropriate additives to make tablets, powders, granules or capsules, e.g., with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

The compounds may be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds may be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, e.g., teaspoonful, tablespoonful, tablet or suppository contains a predetermined amount of the composition containing one or more compounds of the present invention; similarly, unit dosage forms for injection or intravenous administration may comprise the compound of the present invention in a composition as a solution in sterile water, normal saline or another pharmaceutically acceptable carrier.

The term "unit dosage form" as used herein refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, for example vehicles, adjuvants, carriers or diluents, are readily available to the public.

One skilled in the art can easily determine the appropriate method of administration for the exact formulation of the composition being used. Any necessary adjustments in dose can be made readily to meet the nature or severity of the condition and adjusted accordingly by the skilled practitioner.

The actual dose and schedule for drug administration for each patient will be determined by one skilled in the art and will vary depending upon individual differences in pharmacokinetics, drug disposition and metabolism. Moreover, the dose may vary when the compounds are used in combination with other drugs.

The dosage amount of compounds effective for treating memory disorders and learning disorders will generally range from about between 0.1 mg/kg body weight to 100 mg/kg body weight. Specific dosage amounts can be readily ascertained without undue burden and experimentation by those skilled in the art.

REFERENCES

1. Kerwin, R.: Excitatory amino acids and psychosis. In: Excitatory Amino Acids. Eds. R.P. Simon. Theime, NY, pp. 279–283, 1992.
2. Moerschbaecher, J. M.: The role of excitatory amino acids in learning and memory. In: Excitatory Amino Acids. Eds. R. P. Simon. Theime, N.Y., pp. 211–214, 1992.
3. Wroblewski, J. T.; Danyz, W.: Modulation of glutamate receptors: molecular mechanisms and functional implications. Ann. Rev. Pharmacol. Toxicol. 29: 441–447, 1989.
4. Ozawa, S.; Lino, M.; Tsuzuki, K.; Takeuchi, T. Two distinct types of responses to kainate and AMPA in culture hippocampal neurones. In: Excitatory Amino Acids. Ed. R. P. Simon, Theime, N.Y., pp. 117–123, 1992.
5. Sommer, B.; Keinanen, K.; Verdoorm, T. A.; Eisden, W.; Burnashev, N.; Herb A.; Kohler, M.; Takagi, T.; Sakmann, B.; Seeburg, P. H.; Flip and flop: A cell-specific functional switch in glutamate-operated channels of the CNS. Science 249–1580–1585, 1990.
6. Ito, I.; Tanabe, S.; Kohda, A.; Sugiyama, H.: Allosteric potentiation of quisqalate receptors by a nootropic drug aniracetam. J. Physiol. 424: 533–543, 1990.
7. Ozawa, S.; Lino, M.; Abe, M.: Excitatory synapse in the rat hippocampus in tissue culture and effects of aniracetam. Newurosci. Res. 12: 72–82, 1991.
8. Ponetcorvo, M. J.; Evans, H. L.: Effect of aniracetam on delayed matching-to-sample performance of monkey and pigeons. Pharmacol. Biochem and Behaviour 22: 745–752, 1985.
9. Martin, J. R.; Cumin, R.; Aschwaden, W.; Moreau, J. L.; Jenck, F.; Haefely, W.: Aniracetam improves radial maze performance in rats. Neuroreports 3: 81–83, 1992.
10. Werner, L. H.; Halamandaris, A.; Ricca, S.; Dorfman, L.; De Stevens, G.: Dihydrobenzothiadiazein-1,1 -dioxides and their diuretic properties. J. Am. Chem. Soc. 82: 1161–1166, 1960.
11. Topliss, J. G.; Sherlock, M. H.; Reimann, H.; Konzelam, L. M.; Shapiro, E. P.; Pettersen, B. W.; Schneider, H.; Sperber, N.: Antihypertensive agents. I non-diuretic 2H-1, 2,4 benzothiadiazine 1,1-dioxides. J. Med. Chem. 6: 122–127, 1963.
12. Hamill, O. P.; Marty, A.; Neher, E.; Sakmann, B.; Sigworth, F. J.: Improved patch-clamp techniques for high resolution current recording from cells and cell-free membrane patches. Pf lugers Arch. 391: 85–100, 1981.
13. Kant, G. J.; Wright, W. L.; Robinson, T. N.; D'Angelo, C. P.: Effects of MK-801 on learning and memory as assessed using a novel water maze. Pharmacol. Biochem. and Behav. 39: 479–485, 1991.
14. Izquierdo, I.; Medina, H.; GABAA receptor modulation of memory: The role of endogenous benzodiazepines. TIPS 12: 260–265, 1991.
15. Costa, E.: Allosteric modulatory centers of transmitter amino acid receptors. Neuropsychopharmacology 2: 16714 174, 1989.
16. Weiskrantz, L.: Memory—in analyses of behaviour changes. Ed. by L. Weiskrantz. Harper and Row, N.Y., 1968.
17. Honig, W. K.: Studies of working memory in pigeon. In cognitive processes in animal behaviour. Eds. S. H. Hulse and H. Fowler, Hillsdale, N.J., Erlbaum, 1978.
18. Cermak, L. S.; Butter, N.; Goodglass, H.: The extent of memory loss in Korsakoff patients. Neuropsychologia 9: 307–315, 1971.
19. Corkin, S.: Some relationships between global amnesias and the memory impairments in Alzeheimer's disease. In: Aging: Alzeheinmer's Disease: A Report of Progress in Research. Vol. 19. Eds. Corkin, K. L.; Davis, J. H.; Growdon, J. H.; Usdin, E.; Wurtman, R. J., N.Y., Raven Press, 1982.

The invention being this described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method of treating memory disorders and learning disorders which comprises administering to a mammal a need of treatment an effective amount to treat learning disorders or memory disorders of a compound having the formula:

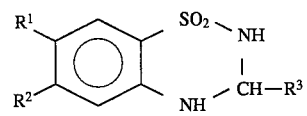

$R^1$ is H or halogen, or $SO_2NH_2$;
$R^2$ is H or halogen;
$R^3$ is $C_1$–$C_8$ straight or branched alkyl,
$C_2$–$C_8$ straight or branched alkenyl, $C_2$–$C_8$ straight or branched alkynyl, $C_1$–$C_8$ straight or branched alkyl, substituted with a halogen, $NH_2$, N-$C_1$–$C_4$-alkyl substituted amine, N,N'-$C_1$–$C_4$-alkyl disubstituted amine, $C_1$–$C_4$-alkoxy group, $C_1$–$C_4$-thioalkyl group, a $C_3$–$C_6$ cycloalkyl group, $C_3$–$C_6$ cycloalkenyl group, a $C_6$–$C_8$-bicycloalkyl or a $C_6$–$C_8$ bicycloalkenyl group, $C_2$–$C_8$ straight or branched alkenyl group substituted with a halogen, $NH_2$, N-$C_1$–$C_4$-alkyl substituted amine, N,N'-$C_1$–$C_4$-alkyl disubstituted amine, $C_1$–$C_4$-alkoxy group, $C_1$–$C_4$-thioalkyl group, a $C_3$–$C_6$ cycloalkyl group, $C_3$–$C_6$ cycloalkenyl group, a $C_6$–$C_8$-bicycloalkyl or a $C_6$–$C_8$ bicycloalkenyl group, $C_2$–$C_8$ straight or branched alkynyl group substituted with a halogen, $NH_2$, N-$C_1$–$C_4$-alkyl substituted amine, N,N'-$C_1$–$C_4$-alkyl disubstituted amine, $C_1$–$C_4$-alkoxy group, $C_1$–$C_4$-thioalkyl group, a $C_3$–$C_6$ cycloalkyl group, a $C_3$–$C_9$-cycloalkenyl group, a $C_6$–$C_8$-bicycloalkyl, or a $C_6$–$C_8$ bicycloalkenyl group, $C_3$–$C_6$ cycloalkyl, $C_3$–$C_6$ cycloalkenyl, $C_6$–$C_8$ bicycloalkyl, or $C_6$–$C_8$ bicycloalkenyl;

with the proviso that when $R^1$ is $SO_2NH_2$ and $R_2$ is halogen, $R^3$ is not $C_6$–$C_8$ bicycloalkenyl; or a pharmaceutically acceptable salt thereof.

2. The method according to claim 1 wherein said compound has the formula:

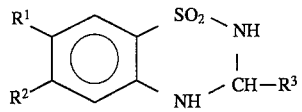

wherein $R^1$ is H; $R^2$ is Cl; and $R^3$ is a $C_1$–$C_8$ straight chain alkyl; or a pharmaceutically acceptable salt thereof.

3. The method according to claim 1 wherein said compound has the formula:

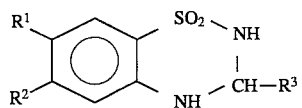

wherein $R^1$ is Cl; $R^2$ is H; and $R^3$ is a $C_1$–$C_8$ straight chain alkyl; or a pharmaceutically acceptable salt thereof.

4. The method according to claim 1, wherein said compound has the formula:

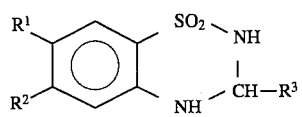

wherein $R^1$ is $SO_2NH_2$; $R^2$ is Cl; and $R^3$ is $C_1$–$C_8$ straight chain alkyl or a pharmaceutically acceptable salt thereof.

5. The method according to claim 2 wherein $R^3$ is $CH_3$.
6. The method according to claim 3 wherein $R^3$ is $CH_3$.
7. The method according to claim 4 wherein $R^3$ is $CH_3$.
8. The method according to claim 2 wherein $R^3$ is $CH_2Cl$ or $CH_2CH_2Cl$.
9. The method according to claim 3, wherein $R^3$ is $CH_2Cl$ or $CH_2CH_2Cl$.
10. The method according to claim 4 wherein $R^3$ is $CH_2Cl$ or $CH_2CH_2Cl$.

11. A method of treating memory disorders and learning disorders which comprises administering to a mammal a need of treatment an effective amount to treat learning disorders or memory disorders of a (+) enantiomer of a compound having the formula:

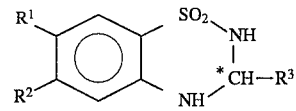

wherein * indicates the chiral carbon atom;

$R^1$ is H or halogen, or $SO_2NH_2$;

$R^2$ is H or halogen;

$R^3$ is $C_1$–$C_8$ straight or branched alkyl, $C_2$–$C_8$ straight or branched alkenyl, $C_2$–$C_8$ straight or branched alkynyl, $C_1$–$C_8$ straight or branched alkyl, substituted with a halogen, $NH_2$, N-$C_1$–$C_4$-alkyl substituted amine, N,N'-$C_1$–$C_4$-alkyl disubstituted amine, $C_1$–$C_4$-alkoxy group, $C_1$–$C_4$-thioalkyl group, a $C_3$–$C_6$ cycloalkyl group, $C_3$–$C_6$ cycloalkenyl group, a $C_6$–$C_8$-bicycloalkyl or a $C_6$–$C_8$ bicycloalkenyl group, $C_2$–$C_8$ straight or branched alkenyl group substituted with a halogen, $NH_2$, N-$C_1$–$C_4$-alkyl substituted amine, N,N'-$C_1$–$C_4$-alkyl disubstituted amine, $C_1$–$C_4$-alkoxy group, $C_1$–$C_4$-thioalkyl group, a $C_3$–$C_6$ cycloalkyl group, $C_3$–$C_6$ cycloalkenyl group, a $C_6$–$C_8$-bicycloalkyl or a $C_6$–$C_8$ bicycloalkenyl group, $C_2$–$C_8$ straight or branched alkynyl group substituted with a halogen, $NH_2$, N-$C_1$–$C_4$-alkyl substituted amine, N,N'-$C_1$–$C_4$-alkyl disubstituted amine, $C_1$–$C_4$-alkoxy group, $C_1$–$C_4$-thioalkyl group, a $C_3$–$C_6$ cycloalkyl group, a $C_3$–$C_6$ cycloalkenyl group, a $C_6$–$C_8$-bicycloalkyl, or a $C_6$–$C_8$ bicycloalkenyl group, $C_3$–$C_6$ cycloalkyl, $C_3$–$C_6$ cycloalkenyl, $C_6$–$C_8$ bicycloalkyl, or $C_6$–$C_8$ bicycloalkenyl;

with the proviso that when $R^1$ is $SO_2NH_2$ and $R^2$ is halogen, $R^3$ is not $C_6$–$C_8$ bicycloalkenyl; or a pharmaceutically acceptable salt thereof.

12. The method according to claim 11 wherein said effective amount is 0.1 to 100 mg/kg body weight.

13. A method at treating memory or learning disorders according to claim 11 which comprises administering to a mammal in need thereof an effective memory and learning enhancing amount of the (+) enantiomer of a compound having the formula:

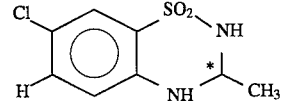

wherein * represents the chiral carbon;

or a pharmaceutically acceptable salt thereof.

* * * * *